United States Patent
Patterson et al.

(10) Patent No.: US 7,569,721 B2
(45) Date of Patent: Aug. 4, 2009

(54) PROCESS FOR CONDUCTING EQUILIBRIUM-LIMITED REACTIONS

(75) Inventors: Leah A. Patterson, Midland, MI (US); Fungau Nmn Ho, Charleston, WV (US)

(73) Assignee: Union Carbide Chemicals and Plastics Technology Corporation, Midland, MI (US)

( * ) Notice: Subject to any disclaimer, the term of this patent is extended or adjusted under 35 U.S.C. 154(b) by 613 days.

(21) Appl. No.: 10/544,817

(22) PCT Filed: Feb. 19, 2004

(86) PCT No.: PCT/US2004/004948

§ 371 (c)(1), (2), (4) Date: Aug. 5, 2005

(87) PCT Pub. No.: WO2004/078679

PCT Pub. Date: Sep. 16, 2004

(65) Prior Publication Data

US 2006/0094895 A1 May 4, 2006

Related U.S. Application Data

(60) Provisional application No. 60/450,746, filed on Feb. 28, 2003.

(51) Int. Cl.
   *C07C 69/52* (2006.01)
   *C07C 67/48* (2006.01)

(52) U.S. Cl. ................................. 560/205; 560/218

(58) Field of Classification Search ............. None
   See application file for complete search history.

(56) References Cited

U.S. PATENT DOCUMENTS

| | | |
|---|---|---|
| 3,776,947 A | 12/1973 | Shimizu et al. |
| 4,280,009 A | 7/1981 | Erpenbach et al. |
| 4,833,267 A | 5/1989 | Nakashima et al. |
| 5,093,520 A | 3/1992 | Nestler et al. |
| 5,231,222 A | 7/1993 | Papa et al. |
| 5,386,052 A | 1/1995 | Sakakura |
| 5,659,072 A | 8/1997 | Bessalem et al. |
| 5,811,574 A | 9/1998 | Exner et al. |
| 5,883,288 A | 3/1999 | Iffland et al. |
| 5,900,125 A | 5/1999 | Exner et al. |
| 5,910,603 A | 6/1999 | Aichinger et al. |
| 6,072,076 A | 6/2000 | Schmidt et al. |
| 6,084,128 A | 7/2000 | Warner et al. |
| 6,348,135 B1 | 2/2002 | Nakahara et al. |
| 6,482,976 B1 * | 11/2002 | Ho et al. ............ 560/205 |

FOREIGN PATENT DOCUMENTS

WO    WO 98/52903 A    11/1998

OTHER PUBLICATIONS

Derwent Abstract, JP 07-307805-A, Tsuiki, et al., Nov. 28, 1995.
Derwent Abstract, JP 08-183756, Chikujo, et al., Jul. 16, 1996.

* cited by examiner

*Primary Examiner*—Paul A Zucker
(74) *Attorney, Agent, or Firm*—Paul D. Hayhurst

(57) ABSTRACT

This invention relates to a process for conducting equilibrium-limited reactions, such as esterification and alcoholysis reactions, that uses two reaction zones. The first reaction zone operates under reaction conditions that retain at least a portion of the product in a liquid phase, and at least a portion of the liquid from the first reaction zone is introduced into a second reaction zone which operates under conditions sufficient to crack heavies, for example, Michael-addition heavies, formed in or introduced into said second reaction zone and to vaporize at least a portion of the product upon production thereof. Such a process allows for removal of product from the reaction system while catalyst desirably remains in the reaction system.

16 Claims, 1 Drawing Sheet

PROCESS FOR CONDUCTING EQUILIBRIUM-LIMITED REACTIONS

CROSS-REFERENCE TO RELATED APPLICATIONS

This application is a 371 of PCT/US2004/004948 filed Feb. 19, 2004, which claims the benefit of U.S. Provisional Application Ser. No. 60/450,746, filed Feb. 28, 2003.

BACKGROUND OF THE INVENTION

This invention pertains to a process for producing a reaction product via equilibrium-limited reactions, such as esterification and alcoholysis (or transesterification) reactions, wherein the process is conducted using two reactor stages and the desired product or products of the equilibrium-limited reactions are removed in the vapor phase, preferably from the second stage reactor.

Equilibrium-limited reactions generally involve the reaction of two or more reactants to produce at least one product and, typically, a coproduct. In order to achieve a greater conversion to the desired product(s), various techniques have been suggested such as removing the coproduct and/or product from the reaction menstruum to maintain a driving force toward the product.

Equilibrium-limited reactions are often conducted in a single reactor with product being selectively removed from the reaction menstruum or in a plurality of reactors in which product is separated from the reaction menstruum in each of the reactor stages. One type of multistage reactor process is disclosed in U.S. Pat. Nos. 5,811,574 and 5,900,125, which disclose a process and an apparatus for the continuous preparation of alkyl esters of (meth)acrylic acid by reacting (meth)acrylic acid and monohydric alkanols of 1 to 8 carbon atoms in the homogeneous, liquid, solvent-free phase at elevated temperatures and in the presence of an acidic esterification catalyst. In the disclosed process, the (meth)acrylic acid, the alkanol and acid catalyst are continuously fed to a reaction zone which consists of a cascade of at least two reaction regions connected in series, and the discharge stream of one reaction region forms a feed stream of a downstream reaction region. The cascade may have from two to four reaction regions spatially separated from one another. These patents disclose an aqueous azeotropic distillation process in which the target alkyl acrylate formed in the reaction zone is separated from the catalyst and starting acid via the top of a rectification zone mounted on the reaction zone as a component of at least one azeotropic mixture consisting of water or water and starting alkanol as further components in addition to the alkyl acrylate. The resulting distillate is separated into at least one organic phase containing the alkyl acrylate and into at least one water-containing aqueous phase. A part of the organic phase containing alkyl acrylate is recycled via the top of the rectification zone. The remaining organic phase, which contains no starting acid, is fed into downstream equipment to isolate the target alkyl acrylate from starting alkanol and other impurities having lower and higher boiling points than the target ester. It is also disclosed that this process is preferably to be used for the preparation of n-butyl acrylate because the boiling points of n-butyl acrylate and acrylic acid are comparatively close together. It is further disclosed that the water content in the water/alkyl acrylate or water/alkanol/alkyl acrylate azeotropic mixtures increases along with the increase of the molecular weight of the alkyl acrylate. Higher energy usage and larger equipment are needed if this azeotropic distillation process is used for the preparation of higher molecular weight acrylates, such as 2-ethylhexyl acrylate.

U.S. Pat. No. 5,883,288 discloses a process for the continuous preparation of alkyl esters of (meth)acrylic acid by reacting (meth)acrylic acid and monohydric alkanols of 1 to 8 carbon atoms in the presence of an acidic esterification catalyst in a reaction zone. The reaction zone can consist of a cascade of at least two reaction regions connected in series, and the discharge stream of one reaction region forms a feed stream of a downstream reaction region. The cascade may have from two to four reaction regions spatially separated from one another. A product mixture is discharged from the reaction zone and fed to a rectification unit (I) and separated into at least one product comprising the alkyl ester of (meth)acrylic acid and one product comprising the catalyst. The alkyl ester of (meth)acrylic acid product is then fed to a further rectification unit (II) and separated off by rectification.

The disadvantage of such a process is that the acid catalyst is sent with the reaction mixture from the reaction zone to a rectification unit (I), rather than being allowed to remain in the reaction zone. The combination of high acid catalyst concentration and high temperatures in the lower section and the bottom of the rectification unit (I) lead to high rates of corrosion, equipment fouling, and undesired side reactions, such as decomposition of the acid catalyst.

Accordingly, an improved process for conducting equilibrium-limited reactions is sought that would minimize and/or eliminate the problems associated with conducting the reactions and with recovering unreacted reactants and product.

SUMMARY OF THE INVENTION

The process of this invention relates to conducting an equilibrium-limited reaction in at least two reaction zones, wherein at least a portion of a liquid phase reaction menstruum containing product produced in a first reactor zone is supplied to a second reaction zone and wherein product produced in the first reaction zone is also produced in the second reaction zone and is removed from the second reaction zone in the vapor phase. The temperature and pressure in the second reaction zone are sufficient to crack heavies, for example, Michael-Addition heavies, formed in or introduced into said second reaction zone and to vaporize at least a portion of the product upon production thereof. Such a process allows for removal of product from the reaction system while catalyst desirably remains in the reaction system. The process of this invention does not require the use of an aqueous azeotropic distillation column to separate the target ester product from the starting acid. While typically only one product is ultimately sought, the process of this invention can simultaneously make two or more products. For instance, acrylic acid may be reacted with a mixture of 2-ethylhexanol and butanol to produce the corresponding 2-ethylhexyl and butyl acrylates.

For the purposes of the present invention, the term "heavies" means compounds having a boiling point higher than that of the target ester product. For a process producing more than one ester product, heavies are compounds having a boiling point higher than the boiling point of the highest boiling ester product. Examples of heavies include oxyesters, such as alkoxy propionates or acryloxy propionates, formed via the Michael-addition reaction of the target ester product with the starting alkanol and/or starting acid.

The process of this invention relates in part to conducting an equilibrium-limited reaction of at least one reactant to produce at least one product, comprising:

a. reacting said at least one reactant in a first reaction zone maintained under reaction conditions, including temperature and pressure, sufficient to produce said at least one product and sufficient to maintain at least a portion of said at least one reactant and said at least one product in the liquid phase;

b. withdrawing a liquid fraction containing said at least one reactant and said at least one product from said first reaction zone, and introducing at least a portion of said withdrawn liquid fraction into a second reaction zone maintained under reaction conditions, including temperature and pressure, sufficient to (i) produce said at least one product, (ii) crack heavies formed in or introduced into said second reaction zone and (iii) vaporize at least a portion of said at least one product upon production thereof;

c. withdrawing an overhead vapor fraction from said second reaction zone, said overhead vapor fraction comprising said at least one product, and introducing at least a portion of said withdrawn overhead vapor fraction into at least one condensation zone to produce said at least one product in the liquid phase;

d. withdrawing a liquid fraction from said at least one condensation zone, said liquid fraction comprising said at least one product and water, and introducing at least a portion of said withdrawn liquid fraction into at least one separation zone to provide by phase separation an organic liquid fraction comprising said at least one product and an aqueous liquid fraction comprising water;

e. withdrawing said organic liquid fraction from said at least one separation zone, said organic liquid fraction comprising said at least one product, and introducing at least a portion of said withdrawn organic liquid fraction into at least one reactant recovery distillation zone to provide an overhead fraction comprising said at least one reactant and a bottoms liquid fraction comprising said at least one product;

f. withdrawing said bottoms liquid fraction from said at least one reactant recovery distillation zone, said bottoms liquid fraction comprising said at least one product, and introducing at least a portion of said withdrawn bottoms liquid fraction into at least one product recovery distillation zone to provide an overhead fraction comprising said at least one product and a bottoms liquid fraction comprising heavies; and g. recovering said at least one product from said withdrawn overhead fraction. In this embodiment, lower purity feed streams, for example, crude 2-ethylhexanol or crude acrylic acid streams containing high concentrations of acrylic acid dimer or other Michael-addition heavies may be utilized in the process of this invention. In one embodiment, heavy residue-containing streams generated from other processes that employ similar equilibrium-limited reactions, for example, integrated equilibrium-limited processes, can be employed as feedstocks. Also, in this embodiment, the product can be efficiently removed from the reaction zone while the catalyst desirably remains in the reaction zone.

The process of this invention also relates in part to conducting an equilibrium-limited reaction of at least one reactant to produce at least one product, comprising:

a. reacting said at least one reactant in a first reaction zone maintained under reaction conditions, including temperature and pressure, sufficient to produce said at least one product and sufficient to maintain at least a portion of said at least one reactant and said at least one product in the liquid phase;

b. withdrawing a liquid fraction containing said at least one reactant and said at least one product from said first reaction zone, and introducing at least a portion of said withdrawn liquid fraction into a second reaction zone maintained under reaction conditions, including temperature and pressure, sufficient to (i) produce said at least one product, (ii) crack heavies formed in or introduced into said second reaction zone and (iii) vaporize at least a portion of said at least one product upon production thereof;

c. withdrawing an overhead vapor fraction from said second reaction zone, said overhead vapor fraction comprising said at least one product, and introducing at least a portion of said withdrawn overhead vapor fraction into at least one condensation zone to produce said at least one product in the liquid phase, and introducing at least one polymerization inhibitor into said at least one condensation zone;

d. withdrawing a liquid fraction from said at least one condensation zone, said liquid fraction comprising said at least one product and water, and introducing at least a portion of said withdrawn liquid fraction into at least one separation zone to provide by phase separation an organic liquid fraction comprising said at least one product and an aqueous liquid fraction comprising water;

e. withdrawing said organic liquid fraction from said at least one separation zone, said organic liquid fraction comprising said at least one product, and introducing at least a portion of said withdrawn organic liquid fraction into at least one reactant recovery distillation zone to provide an overhead fraction comprising said at least one reactant and a bottoms liquid fraction comprising said at least one product, and introducing at least one polymerization inhibitor into said at least one reactant recovery distillation zone;

f. withdrawing said bottoms liquid fraction from said at least one reactant recovery distillation zone, said bottoms liquid fraction comprising said at least one product, and introducing at least a portion of said withdrawn bottoms liquid fraction into at least one product recovery distillation zone to provide an overhead fraction comprising said at least one product and a bottoms liquid fraction comprising heavies, and introducing at least one polymerization inhibitor into said at least one product recovery distillation zone;

g. withdrawing from said at least one product recovery distillation zone a bottoms fraction comprising at least one polymerization inhibitor and supplying at least a portion of the withdrawn bottoms fraction to said at least one condensation zone, said at least one reactant recovery distillation zone, said at least one product recovery distillation zone and a water removal distillation zone, in an amount sufficient to minimize or eliminate polymerization of said at least one reactant and said at least one product; and h. recovering said at least one product from said withdrawn overhead fraction. In this embodiment, polymerization inhibitors are reused in the process by recycling the withdrawn bottoms fraction containing polymerization inhibitors from the at least one product recovery distillation zone to the at least one condensation zone, the at least one reactant recovery distillation zone, the at least one product recovery distillation zone and the water removal distillation zone. In addition to being cost effective, the recycling of polymerization inhibitors to the various distillation zones controls undesirable polymerization. For example, reactive monomers such as acrylic acid and 2-ethylhexyl acrylate readily form polymer via free radical polymerization if not well inhibited. This process is further cost effective in that the recycle stream returns heavies to the second reaction zone for cracking.

In another embodiment, the above process also comprises generating in the first reaction zone and, under reaction conditions of the first reaction zone, a vapor fraction comprising water, at least a portion of the one reactant and at least a portion of the one product, withdrawing the vapor fraction from the first reaction zone and introducing the vapor fraction into at least one water removal distillation zone, withdrawing the overhead vapor fraction from the at least one water removal distillation zone, introducing at least a portion of the withdrawn overhead vapor fraction into at least one condensation zone to produce a liquid fraction, withdrawing the liquid fraction from the at least one condensation zone, the liquid fraction comprising water, at least a portion of the one reactant and at least a portion of the one product, introducing at least a portion of the withdrawn liquid fraction into at least one separation zone to provide by phase separation an organic liquid fraction comprising the at least a portion of the at least one reactant and at least a portion of the at least one product and an aqueous liquid fraction comprising water; and withdrawing the organic liquid fraction from the at least one separation zone, the organic liquid fraction comprising at least a portion of the at least one reactant and at least a portion of the at least one product, and recycling at least a portion of the withdrawn liquid fraction to the at least one water removal distillation zone. In this embodiment, water generated in the first reaction zone is effectively removed from the first reaction zone.

The unique configuration of the first and second reaction zones, condensation zone, separation zone and reactant recovery distillation zone is advantageous in enabling the production of a bottoms liquid fraction (from the reactant recovery distillation zone) having high concentrations of 2-ethylhexyl acrylate, for example, at least 50.0 weight percent, and having essentially no acrylic acid. This process allows for removal of product from the reaction zone while catalyst desirably remains in the reaction system. The process of the invention does not require the use of an aqueous azeotropic distillation column to separate the desired ester product from the starting acid.

The process of this invention is particularly applicable in the production of esters, especially esters that contain ethylenic unsaturation or other reactive groups that can lead to unwanted side reactions. Advantageous processes include the formation of alkyl acrylates and alkyl methacrylates from alkanols of 4 to about 12 carbon atoms, and acrylic acid or methacrylic acid. A preferred aspect of this invention pertains to processes for making 2-ethylhexyl acrylate from 2-ethylhexanol and acrylic acid.

DESCRIPTION OF THE PREFERRED EMBODIMENTS

Figure 1:
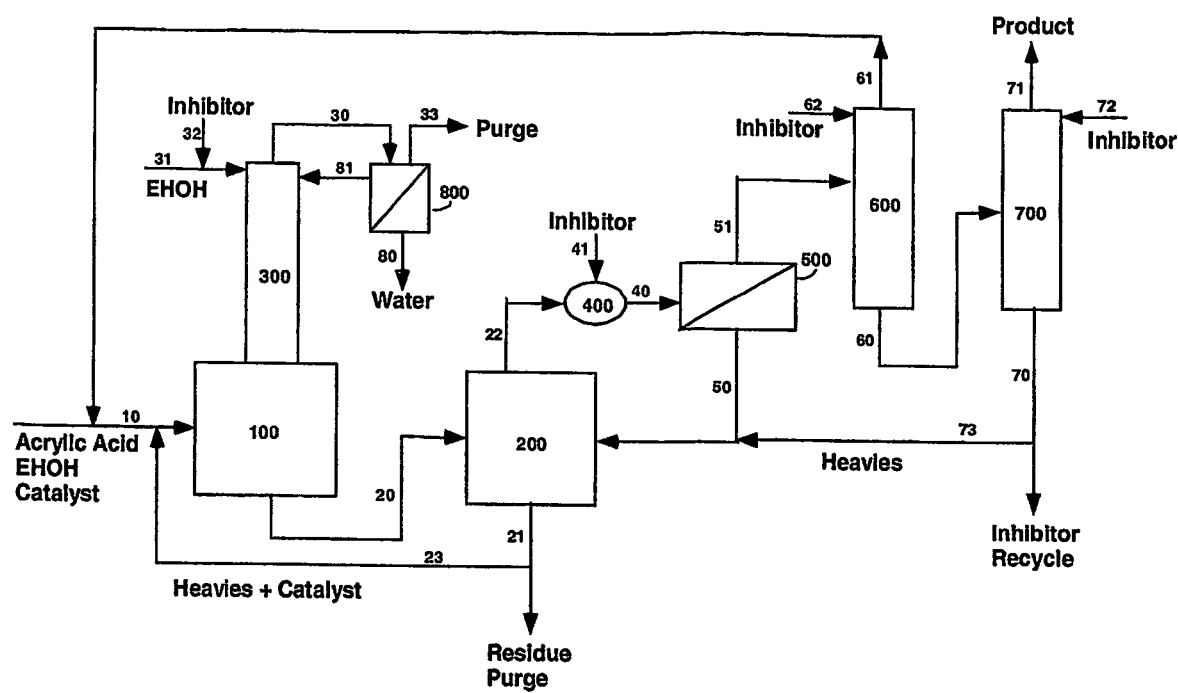
FIG. 1 is a schematic depiction of a process for making 2-ethylhexyl acrylate from acrylic acid and 2-ethylhexanol in accordance with one embodiment of this invention.

This invention relates to a process for conducting equilibrium-limited reactions. This invention pertains broadly to any equilibrium-limited reaction process; however, the process is most useful for producing organic equilibrium products, especially esters. The process can be conducted batchwise, but preferably is employed as a continuous process in which the reactants and any adjuvants, such as catalysts, inhibitors and solvents, are added periodically or uninterruptedly to, and products are removed periodically or uninterruptedly from, the reaction zones. The following discussion references the use of at least two reactants for the sake of convenience. It should be understood in the aspects of this invention where a single reactant is used for the equilibrium-limited reaction, that the description applies equally. Similarly, reference is made to a co-product for the sake of convenience. Equilibrium-limited reactions where no co-product is formed are also encompassed by the invention.

Typical equilibrium-limited reaction processes include esterification and alcoholysis reactions. Esterification reactions involve the production of an ester by reaction of an alcohol with a carboxylic acid. A coproduct, water, is also produced. In alcoholysis (transesterification) reactions, an ester is reacted with an alcohol with an interchange occurring.

The carboxylic acids used in the process of this invention often can be represented by the formula R'C(O)OH, wherein R' is a hydrocarbyl-containing group of 1 to about 8, preferably 1 to about 4, carbon atoms and may be saturated or unsaturated aliphatic or cycloaliphatic (including branched and unbranched aliphatic and cycloaliphatic which may be saturated or contain ethylenic unsaturation), aryl, alkaryl (cyclic, linear and branched alkyl), aralkyl (cyclic, linear and branched alkyl), or any of the preceding containing a hetero atom such as oxygen, sulfur, nitrogen and phosphorus, and R' may be substituted with one or more hetero atom-containing substituents such as halides. In alcoholysis processes, the esters generally can be represented by the formula R'C(O)OR" wherein R' is as defined above and R" is a hydrocarbyl-containing group of 4 to about 12, preferably 4 to about 8, carbon atoms and may be saturated or unsaturated aliphatic or cycloaliphatic (including branched and unbranched aliphatic and cycloaliphatic which may be saturated or contain ethylenic unsaturation), aryl, alkaryl (cyclic, linear and branched alkyl), aralkyl (cyclic, linear and branched alkyl), or any of the preceding containing a hetero atom such as oxygen, sulfur, nitrogen or phosphorus. The alcohols can be represented by the formula R'''OH wherein R''' is a hydrocarbyl-containing group of 4 to about 12 carbon atoms and may be saturated or unsaturated aliphatic or cycloaliphatic, aryl, alkaryl, aralkyl, or any of the preceding containing a hetero atom such as oxygen, sulfur, nitrogen or phosphorus, and R''' may be substituted with one or more heteroatom-containing substituents such as halides, with the proviso that in an alcoholysis reaction, R''' is other than R". The products can be represented by the formula R'C(O)OR'''.

The process of this invention can be used to simultaneously produce more than one equilibrium product. For instance, more than one acid or ester can be used or more than one alcohol can be used to form a mixture of esters. By the use of two reaction zones operating under different conditions, a product stream containing one ester product may be recovered from the primary reaction zone and a higher boiling ester product may be recovered from the secondary reactor. Alternatively, both products may be recovered from the secondary reaction zone, either both in a vapor stream or one in the vapor stream and the other in a liquid product stream.

Particularly attractive uses of the process of this invention are in the production of acetates, acrylates, propionates and methacrylates wherein R''' is 4 to about 12 carbons, preferably 4 to 11, more preferably 4 to 8, and most preferably 5 to 8, carbon atoms. Examples of suitable alcohols include n-butanol, isobutanol, pentanol, hexanol, 2-ethyl hexanol, methoxypropanol, ethoxyethanol, methoxybutanol, ethoxypropanol, ethoxybutanol, butoxyethanol, butoxyethoxyethanol, ethoxyethoxyethanol, and methoxyethoxyethanol. The carboxylic acid feed preferably contains 2 to 4 carbons.

Examples of preferred carboxylic acids include acetic acid, acrylic acid, propionic acid, and methacrylic acid.

The process is conventionally conducted at temperatures within the range of from about 0° to about 200° C., preferably in the range of from about 40° to about 150° C., but below a temperature that causes undue degradation of reactants, desired products, or any catalyst used. Temperatures that are too low result in lower reaction rates and temperatures that are too high result in more by-products and have higher corrosion rates. The second reaction zone temperature (together with pressure) should be sufficient to crack heavies, for example, Michael-addition heavies, formed in or introduced into the second reaction zone and to vaporize at least a portion of the ester product upon production thereof. However, the second reaction zone temperature should not cause undue degradation of reactants, desired products, or any catalyst used. Where a reactant contains another reactive group, for example, unsaturation in the case of acrylic and methacrylic moieties, the temperature should be below that which causes undesirable side reactions. To some extent, the polymerization reactions can be controlled by the use of inhibitors, and thus the operating temperature of the reaction zones will also be influenced by inhibitor concentration.

The pressure under which equilibrium-limited reactions can be conducted can also vary widely. Typically, pressures range from subatmospheric to superatmospheric, for example, from about 0.01 to about 100 bar, most often from about 0.02 to about 10 or about 15 bar absolute. As indicated above, the second reaction zone temperature and pressure should be sufficient to crack heavies, for example, Michael-addition heavies, formed in or introduced into the second reaction zone and to vaporize at least a portion of the ester product upon production thereof.

The reaction is conducted in the presence of a liquid medium. One or more of the reactants, products, coproducts and side reaction products can make up the liquid medium for the reaction. The liquid medium can optionally comprise a solvent. The reaction menstruum in the first reaction zone preferably is different than that in the second reaction zone. Where a solvent is used, it is preferably substantially inert under reaction conditions.

Many equilibrium-limited reactions employ a catalyst. Catalysts appropriate for the equilibrium-limited reaction can be used in the processes of this invention. For esterification, catalysts are often acids such as sulfuric acid, sulfonic acids and acidic exchange resins, and for alcoholysis reactions, metal oxides and alkoxides such as of alkali, alkaline earth, transition and rare earth metals, lead, bismuth and tin and the like. The catalyst is used in a catalytic amount, and the amount of catalyst can vary widely. Homogeneous catalysts are often used in the range of from about 0.001 to about 10 or about 20 weight percent of the liquid menstruum, and heterogeneous catalysts typically comprise from about 10 to about 60 percent of the volume of the reaction zone. Lower catalyst concentrations result in lower esterification and cracking rates and a higher purge from the first and/or second reaction zones. Higher catalyst concentrations generally make more by-products and have higher corrosion rates. When employing sulfonic acid catalysts such as dodecylbenzene sulfonic acid (DBSA), a small amount of water should be present, for example, from about 0.01 weight percent or less to about 1 weight percent or greater, preferably less than about 1 weight percent, in the first and/or second reaction zones to minimize the formation of the sulfonate ester.

Other adjuvants may be contained in the liquid reaction media, such as antioxidants, stabilizers, buffers, polymerization inhibitors and the like. Phenothiazine (PZ) is the preferred inhibitor. Since PZ is not soluble in water, hydroquinone (HQ) is preferably used as the inhibitor for aqueous streams. The monomethyl ether of hydroquinone (MEHQ) is the preferred product shipping inhibitor and is used in the product recovery distillation column. Air or oxygen is used to enhance the effectiveness of the inhibitors. A partial pressure of oxygen of from about 0.05 to about 1.0, preferably from about 0.1 to about 0.8, mm Hg at the column base is preferred for all the columns.

The process of this invention is conducted in at least one first reaction zone and at least one second reaction zone. The at least one first reaction zone preferably is maintained under reaction conditions such that at least a portion of the at least two reactants and at least one product are maintained in the liquid phase. Preferably, under the conditions of the first reaction zone including any azeotrope formation, the vapor-liquid equilibrium for the at least one product is such that at least about 70, preferably at least about 80, percent of the product in the first reaction zone is in the liquid phase. Preferably, under the conditions of the first reaction zone including any azeotrope formation, the vapor-liquid equilibrium for the at least two reactants is such that at least about 50, preferably at least about 70, percent of each reactant in the first reaction zone is in the liquid phase.

The first reaction zone may be a single vessel or may comprise two or more discrete vessels, one or more of which may be a stirred or agitated tank. The first reaction zone is operated under conditions such that essentially no cracking occurs in the first reaction zone. In one embodiment, an overhead stream may be taken to remove co-product (for example, water, from the esterification of alcohol with carboxylic acid) and thus drive the reaction further toward conversion to the desired product. Generally, the overhead stream is subjected to rectification or other separation unit operation such as liquefaction, condensation and liquid phase separation, sorption and membrane separation, to recover reactants for recycle to the reaction zone. In another embodiment, no overhead stream is removed from the first reaction zone, thus permitting the use of a plug flow reactor. Because no overhead stream need be taken, savings in equipment and energy can be achieved.

Generally, the residence time of the liquid menstruum in the first reaction zone is sufficient to yield production in a concentration within 50, typically within about 70, and sometimes at least about 90 or 95, percent of the theoretical equilibrium concentration of the product in the reaction menstruum under the conditions of the reaction (for given reactant concentrations). Advantageously, at least about 50, preferably at least about 70, and most preferably between about 75 and 95, percent of the total amount of product produced in the process is produced in the first reaction zone.

The relative amounts of the reactants fed to the first reaction zone may also vary widely and will often be selected based upon economic factors. In many commercial equilibrium-limited reaction processes, the reactants are fed in an approximately stoichiometric ratio for producing the desired product, plus any additional amounts required to make up for losses due to side reactions. Often, for esterification and alcoholysis reactions, the mole ratio of the alcohol to acid or ester is from about 0.9:1 to about 1.1:1. Preferably, the first reaction zone is operated such that an amount equivalent to at least about 50, preferably at least about 70, and most preferably between about 75 and 95, percent of the fresh feed of at least one of the reactants is consumed. It should be understood that the amount of the reactants, and their relative concentrations, in the first reaction zone may be different than that of the fresh feed due to recycling of unreacted reactants. Generally, any recycle of reactants is to the first reaction zone in order to enhance the driving force to the desired product.

Liquid is withdrawn from the first reaction zone, which liquid contains product and reactants. At least a portion of this liquid is introduced into a second reaction zone. While in many instances, essentially all of the liquid withdrawn from the first reaction zone is passed to the second reaction zone, the broad concept of this invention contemplates, for instance, an intervening separation step to be used to remove product and/or coproduct from the liquid. The separation may simply be a liquid phase separation to remove, for example, water from an esterification, a flashing or distillation unit operation, or product or coproduct via a membrane separation or a sorption step. Also, a portion of the liquid stream may be used for other processing. Additional reactant can be provided to the second reaction zone as a fresh feed or through recycle.

Like the first reaction zone, the second reaction zone may be a single vessel or may comprise two or more discrete vessels. The conditions of the second reaction zone are maintained such that the product is preferably produced in the liquid phase and then vaporized. Preferably, a boiling point reducing agent, preferably water, is present to lower the boiling point of the product to avoid deleterious effects of high temperatures or expensive, high vacuum.

Preferably, under the conditions of the second reaction zone, the vapor-liquid equilibrium for the at least one product is such that less than about 50, preferably less than about 30, percent of the product in the second reaction zone is in the liquid phase. In many instances, under the conditions of the second reaction zone, the vapor-liquid equilibrium for the at least two reactants results in at least one reactant being vaporized so that less than about 50, and sometimes less than about 30, percent of at least one of, sometimes both, the reactants in the second reaction zone are in the liquid phase. Generally at least about 5, typically at least about 10, and as much as about 50, percent of the fresh reactant fed to the reaction system that is consumed in the reaction system is consumed in the second reaction zone.

Often the reactions in the second reaction zone are conducted at temperatures within the range of from about 0° to about 200° C., more typically from about 40° to about 170° C., but below a temperature that causes undue degradation of the reactants, desired products, catalyst or desirable side reactions. The second reaction zone temperature (together with pressure) should be sufficient to crack heavies, for example, Michael-addition heavies, formed in or introduced into the second reaction zone and to vaporize at least a portion of the ester product upon production thereof. Where a reactant contains another reactive group, for example, unsaturation in the case of acrylic and methacrylic moieties, the temperature should also be below that which causes undesirable side reactions such as polymerization. Polymerization inhibitors may be used to extend the desirable temperature range for the reaction. The pressure in the secondary reaction zone can also vary widely. Typically, pressures range from subatmospheric to superatmospheric, for example, from about 0.01 to about 100 bar, most often from about 0.02 to about 10 or about 15 bar, absolute.

The reaction in the second reaction zone is conducted in the presence of a liquid comprising at least one of: (A) at least one of said reactants; (B) a product other than the substantially vaporized product, where more than one product is intended to be formed; (C) a co-product other than a substantially vaporized co-product, and (D) at least one other liquid component, for example, a solvent. Vapor is withdrawn from the second reaction zone and comprises (i) at least one of the reactants, (ii) the product, and (iii) the co-product, if any.

Where the equilibrium-limited reaction is an esterification or alcoholysis reaction, it is possible for the acid or ester to dimerize or generate other heavies. For the esterification of acrylic acid and 2-ethylhexanol to form 2-ethylhexyl acrylate, the heavies are formed by a Michael-addition reaction. The dimer or heavies product is typically an equilibrium product. The process of this invention facilitates cracking of the dimer and other heavies. Particularly, the second reaction zone can be operated at sufficiently high temperatures to crack the dimer and heavies, and the dimer and heavies may comprise a substantial portion of the liquid menstruum, for instance, at least about 10 or, more typically, about 20 to about 90 or more, weight percent of the menstruum. The heavy residues, including uncrackable heavies, polymerization inhibitors, catalyst and polymers, are purged via the second reaction zone tails.

In one embodiment, the process of the invention further comprises withdrawing a bottoms liquid fraction from the second reaction zone, said bottoms liquid fraction comprising heavies, inhibitors and catalyst, and recycling at least a portion of said withdrawn bottoms liquid fraction to at least one of the first and/or second reaction zones.

In another embodiment, the process comprises withdrawing an overhead vapor fraction from a reactant recovery distillation zone, said overhead vapor fraction comprising at least one reactant, introducing at least a portion of said withdrawn overhead vapor fraction into at least one condensation zone to produce said at least one reactant in the liquid phase, and recycling at least a portion of at least one reactant in the liquid phase to at least one of the first and/or second reaction zones.

It is also contemplated that the process can comprise withdrawing a bottoms liquid fraction from at least one product recovery distillation zone, said bottoms liquid fraction comprising heavies, and recycling at least a portion of said withdrawn bottoms liquid fraction to at least one of the first and/or second reaction zones.

The process of the invention can be operated such that water is produced in the first reaction zone and, under reaction conditions of said first reaction zone, a vapor fraction comprising water, at least a portion of said at least one reactant and at least a portion of at least one product, is generated and said vapor fraction is withdrawn overhead from said first reaction zone and introduced into at least one water removal distillation zone.

The process of the invention can also be operated in a manner such that at least a portion of at least one reactant is introduced into the top half of a water removal distillation column.

The process of this invention will be further described with respect to the esterification of acrylic acid with 2-ethylhexanol. While this is a preferred manner to produce 2-ethylhexyl acrylate, it is not intended to limit the broader aspects of this invention.

As a brief overview, 2-ethylhexyl acrylate is prepared by acid catalyzed esterification of acrylic acid with 2-ethylhexanol. In the process acrylic acid is esterified with a homogeneous acidic catalyst in two reactors run in series. In the first reactor, water is removed overhead. The tails stream containing 2-ethylhexyl acrylate, unreacted reactants, and by-product is sent to a second reactor in order to increase conversion and crack heavies. 2-Ethylhexyl acrylate, unreacted reactants, and by-products, are recovered in the overhead make of the second reactor. This overhead make is refined to give essentially pure 2-ethylhexyl acrylate.

With reference to FIG. 1, fresh acrylic acid is fed via line 10 to a first reactor 100. Fresh 2-ethylhexanol can be fed directly to reactor 100 via line 10 and/or indirectly via line 31 and/or lines 62 and 61. The molar ratio of fresh 2-ethylhexanol to fresh acrylic acid preferably is from about 0.9:1 to about 1.1:1. The acrylic acid and 2-ethyl hexanol supplied to the reactor 100 are typically of standard purities. However, as a result of the processes of the present invention, higher concentrations of typical impurities in the acrylic acid stream are better tolerated. For example, the acrylic acid feed to reactor 100 may contain up to 2 or more weight percent acrylic acid dimer, an impurity commonly present in the acrylic acid feed. Acrylic acid dimer is readily cracked by the high temperature operation of the second reactor 200 as discussed herein. Similarly, as a result of the unique refining scheme, it is possible to easily remove alkanol-derived impurities, which allows the use of a lower grade alkanol feed. The ability to use a wide range of acid and alcohol leads to significant economic savings.

The reaction is carried out in the presence of an acidic catalyst that is introduced via line 10 into reactor 100. Illustrative acidic catalysts include, for example, sulfuric acid, phosphoric acid, and resins that contain acid functional groups. Preferably, the catalyst is a long chain alkyl benzene sulfonic acid such as dodecylbenzene sulfonic acid (DBSA). DBSA catalyst and variations of it are described in U.S. Pat. No. 5,231,222, the disclosure of which is incorporated herein by reference. Relative to other catalysts, DBSA generates significantly less impurities and heavies during the esterification of acrylic acid with 2-ethylhexanol; hence, higher efficiencies are achieved with DBSA as a result of low impurity and heavies formation. DBSA is a homogeneous catalyst. Nonetheless, the reaction is carried out using DBSA because, unlike conventional process employing DBSA, which would require catalyst reclamation steps, in the present processes DBSA is simply cycled via lines 21 and 23 between reactors 100 and 200. The reactors 100 and 200 and supply lines 10, 20, 21 and 23 are constructed of materials resistant to corrosion by the acid catalyst.

In reactor 100 the amount of DBSA preferably is from about 0.1 to about 10, more preferably from about 0.5 to about 2, weight percent of the liquid menstruum. DBSA is purged from the process during normal operation, thus the catalyst make-up to reactor 100 or 200 can be as pure catalyst or as a solution of the catalyst with acrylic acid, 2-ethylhexanol, recycle liquid or any other process stream.

It is well known in the art that chemical inhibitors are employed to inhibit the formation of polymers derived from acrylic acid and/or 2-ethylhexyl acrylate. Inhibitors are provided to reactor 100 through the water removal distillation column 300, preferably via introduction into the top half of that column. The inhibitors include phenothiazine (PZ), hydroquinone (HQ), and the monomethyl ether of hydroquinone (MEHQ). It is generally accepted that polymer formation occurs in areas where the temperature is high, such as the reactor and distillation columns, or in those areas where vapor condenses on cold surfaces. PZ is utilized in organic streams and HQ and/or MEHQ in water streams. The amount of inhibitors used depends on the process. The concentration of chemical inhibitors in reactor 100 will be from about 50 to about 30,000, for example, about 10,000, ppm by weight based upon the weight of the liquid menstruum.

Besides the chemical inhibitors, oxygen is added to reactor 100 to enhance the inhibition of polymer formation. The use of oxygen is well known in the art. The oxygen can be added as pure oxygen, as a mixture with an inert gas, or preferably as air. The oxygen is supplied by an air sparger provided at the bottom of the reactor (not shown).

Reactor 100 is a tank type reactor for the reaction of acrylic acid with 2-ethylhexanol and is designed to allow the removal of water in order to force the reaction equilibrium to acrylate. A conversion of about 70 to about 85 percent is desired. A portion of the liquid in reactor 100 is taken to a reboiler (not shown) for increasing the temperature of the liquid. The reboiler can be a conventional tube in shell vessel. The volume turnover rate through the reboiler must assure that the contents of the reactor are well agitated and uniformly heated. Alternatively, a jacketed reactor designed to generate the requisite heat and provided with mechanical stirrers could be used in place of the tank reactor and reboiler.

The temperature in reactor 100 can range from about 80 to about 170° C. but it is most preferred to maintain the temperature within the range of from about 100 to about 130° C. The return stream from the reboiler is therefore at a temperature about 5 to about 15° C. higher. The average residence time in reactor 100 preferably is from about 1 to about 6 hours. The pressure in reactor 100 preferably is maintained at from about 100 to about 1000 mm Hg (0.13 to 1.33 bar) absolute. The liquid in reactor 100 preferably contains less than 1 weight percent water and preferably is in a single phase.

The esterification reaction generates water which is removed overhead and supplied to the bottom of a water removal distillation column 300. As stated above, removing water drives the reaction toward 2-ethylhexyl acrylate. The distillation column 300 may be attached to the top of the reactor. Distillation column 300 is of standard engineering design and can use trays or packing. To accommodate any entrainment of the DBSA catalyst, the bottom trays may need to be constructed of a metal which can handle highly corrosive liquid. To prevent polymerization and other fouling reactions in the distillation column 300, conventional inhibitors such as hydroquinone and phenothiazine are introduced via lines 31 and 32 into column 300, diluted by 2-ethylhexanol or some other process liquid. Instead of feeding the alkanol starting material directly into reactor 100, at least a portion of the alkanol starting material may be introduced into the top section of distillation column 300.

The overhead from the distillation column 300 is removed as a vapor via line 30 and supplied to a condenser (not shown) and then to separator 800, which preferably is a decanter. In the condenser, the vapor is condensed and the resulting liquid is phase separated in separator 800, with a portion of the organic phase being returned via line 81 to the distillation column 300 and the remainder of the organic phase being purged to remove any undesired low-boiling impurities and by-products, and the aqueous phase being sent via line 80 to disposal or to another separation device (not shown) to recover organics from the aqueous phase.

The liquid reaction menstruum from the reactor 100 is supplied via line 20 to reactor 200. Reactor 200 is a standard tank reactor equipped with an air sparger (not shown). A portion of the liquid in reactor 200 is taken to a reboiler (not shown) to increase the temperature of the liquid. The volume turnover rate through the reboiler must assure that the contents of the reactor are well agitated and maintained at the desired temperature.

The operating temperature in reactor 200 is higher than reactor 100 and the preferred range is from about 115° C. or about 135° C. to about 150° C. The return stream from the reboiler is about 5° C. to about 15° C. higher than the preferred reactor temperature. The higher temperature not only facilitates the conversion of the remaining 2-ethylhexanol and acrylic acid to product, but very importantly, under these conditions, enable the heavies to be cracked back to 2-ethylhexyl acrylate, acrylic acid and 2-ethylhexanol.

The operating pressure in reactor 200 preferably is lower than the pressure in reactor 100, and the preferred range is about 10 to 200 mm Hg absolute (about 0.01 to 0.26 bar absolute). The residence time in reactor 200 is from about 1 to about 6 hours. Water is fed to reactor 200 in order to maintain a concentration of about 1 weight percent of the liquid menstruum for effective catalyst operation, and to facilitate vaporization of 2-ethylhexyl acrylate. The concentration of DBSA in the second reactor is about 1 to about 20, preferably about 5 to about 15, for example, about 10, weight percent based upon the weight of the liquid menstruum. As with reactor 100, inhibitor is added throughout reactor 200 to reduce polymerization.

The liquid bottom stream from reactor 200, which contains heavies and catalyst, is recycled via lines 21 and 23 to reactor 100. The bottom stream from reactor 200 is richer in catalyst and heavies than reactor 100. It should also be noted that the inhibitor concentration is also greater than in the first reactor, due to the cycle of the heavies between reactors 100 and 200. A purge from this recycle stream can be taken via line 21. The unique reaction system of this process allows for the recycle of heavies, catalyst and inhibitors. In conventional processes the entire heavies stream containing the catalyst and inhibitors is typically discarded. Thus, the processes of this invention enable lower catalyst and inhibitor usage and reduced inhibitor and catalyst cost.

2-Ethylhexyl acrylate, water and unreacted acrylic acid and 2-ethylhexanol are removed as a vapor from reactor 200 and supplied via line 22 to condenser 400 and then to separator 500. Separator 500 preferably is a decanter. Either fresh or recycled inhibitor is introduced via line 41 into condenser 400. In condenser 400, the vapor is condensed and the resulting liquid is supplied via line 40 to separator 500 where it is phase separated, with the organic phase being supplied via line 51 to reactant recovery distillation column 600 and at least a portion of the aqueous phase being sent via line 50 to reactor 200. Either fresh or recycled inhibitor is introduced via line 62 into distillation column 600. The primary purpose of distillation column 600 is to separate the organic liquid stream from separator 500 into a tails fraction containing 2-ethylhexyl acrylate and heavies, and an overhead stream comprising 2-ethylhexanol and acrylic acid. The tails fraction is essentially free of 2-ethylhexanol and acrylic acid. The column design is consistent with conventional engineering practice and can use packing or trays. In this embodiment, the base temperature of distillation column 600 is from about 120 to about 160° C. with a pressure of about 10 to about 100 mm Hg (0.01 to 0.13 bar absolute). The overhead stream from distillation column 600 is recycled via line 61 back to either or both of reactors 100 and 200.

The tails fraction from distillation column 600 is supplied via line 60 to product recovery distillation column 700. Fresh inhibitor is introduced via line 72 into distillation column 700. Column 700 separates the tails fraction into an overhead stream of 2-ethylhexyl acrylate and a tails stream of heavies. The tails stream is recycled via lines 70 and 73 to either or both of reactors 100 and 200. The tails stream also contains inhibitors which, as described earlier, are desirably recycled. The column design is consistent with conventional engineering practice and can use packing or trays. The base temperature of the column is about 120 to about 160° C. with a pressure of about 10 to about 100 mm Hg (0.01 to 0.13 bar absolute). Alternatively, a vapor stream can be withdrawn from the bottom portion or base of column 600 and condensed to form a stream of 2-ethylhexyl acrylate, thus eliminating the need for distillation column 700.

As stated above, the process of this invention can be used to make other products from equilibrium-limited reactions. In the following example, 2-ethylhexyl acrylate is produced by a process in accordance with this invention. All parts and percentages are by weight unless otherwise indicated.

EXAMPLE 1

This process scheme of this example is shown in FIG. 1. A total of 379 g/h of fresh 2-ethylhexanol, 352 g/h via line 31 and 27 g/h via lines 62 and 61, and 215 g/h of fresh acrylic acid, via line 10, are fed continuously to a first reactor (100). The molar ratio of fresh 2-ethylhexanol to fresh acrylic acid is about 1 to 1. Unreacted 2-ethylhexanol and acrylic acid are recycled through line 61 to reactor 100 at 172 g/h; the recycle stream contains 30 percent acrylic acid, 42 percent 2-ethylhexanol, 19 percent 2-ethylhexyl acrylate, 4 percent water, and 5 percent other compounds. Recycle inhibitor solution is fed through line 32 at 22 g/h. Fresh dodecylbenzene sulfonic acid catalyst is fed to reactor 100 through line 10 at about 1 g/h, along with 55 g/h recycle catalyst solution from a second reactor (200) through line 23. Reactor 100 is operated at a temperature of 125° C. and a pressure of 310 mm Hg absolute. The residence time in reactor 100 is from about 4.5 to about 5.5 hours. A vapor stream rich in water is removed from reactor 100 and sent to a water removal column (300), which is operated at a head pressure of 300 mm Hg absolute. The overhead vapor from column 300 is condensed in a condenser (not shown) and decanted in a separator (800). The aqueous phase is removed through line 80 at a rate of 55 g/h. A portion of the organic phase is returned to column 300 via line 81 and the remaining is removed via line 33 at a rate of 3 g/h to purge undesired low-boiling impurities and by-products. A 786 g/h reaction liquid, containing about 1% dodecylbenzene sulfonic acid catalyst and about 0.5% water, is discharged from reactor 100 and fed to reactor 200 through line 20.

Reactor 200 is operated at a temperature of 130° C., a pressure of 40 mm Hg absolute, and a residence time of 2.5 to 3.5 hours. The dodecylbenzene sulfonic acid catalyst concentration in reactor 200 is about 10% and the water concentration in reactor 200 is about 0.1%. Water is fed to reactor 200 through line 50 at a rate of 255 g/h. A vapor stream is removed from reactor 200 through line 22, condensed in a condenser (400) and decanted in a separator (500). The organic phase from separator 500 is fed to a reactant recovery column (600) via line 51 at a rate of 762 g/h. The aqueous phase from separator 500 is returned to reactor 200 via line 50. Fresh inhibitor solution is fed to condenser 400 through line 41 at 6 g/h along with 33 g/h recycle inhibitor solution. A residue purge stream is removed from reactor 200 via line 21 at a rate of 8 g/h.

Reactant recovery column 600 is operated at a head pressure of 75 mm Hg absolute, a head temperature of about 110° C. and a base temperature of about 145° C. Unreacted reactants are recovered as a distillate and recycled to reactor 100 through line 61. A liquid stream, which is essentially free of 2-ethylhexanol and acrylic acid, is recovered from the base of column 600 at a rate of 590 g/h and fed to a product recovery column (700) via line 60. Fresh inhibitor solution, using fresh 2-ethylhexanol as inhibitor carrier, is fed to column 600 through line 62 at a rate of 27 g/h.

Product recovery column 700 is operated at a head pressure of 18 mm Hg absolute, a head temperature of about 120° C. and a base temperature of about 125° C. Refined 2-ethylhexyl acrylate is recovered as a distillate at a rate of 549 g/h with a purity of 99.7 percent. A liquid stream is removed from the bottom at a rate of 55 g/h and used as recycled inhibitor solution for column 300 and condenser 400. Fresh inhibitor solution, using pure 2-ethylhexyl acrylate as inhibitor carrier, is fed to column 700 through line 72 at a rate of 14 g/h.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

What is claimed is:

1. A process for conducting an equilibrium-limited reaction of at least one reactant to produce at least one product, comprising:
    a. reacting said at least one reactant in a first reaction zone maintained under reaction conditions, including temperature and pressure, sufficient to produce said at least one product and sufficient to maintain at least a portion of said at least one reactant and said at least one product in the liquid phase;
    b. withdrawing a liquid fraction containing said at least one reactant and said at least one product from said first reaction zone, and introducing at least a portion of said withdrawn liquid fraction into a second reaction zone maintained under reaction conditions, including temperature and pressure, sufficient to (i) produce said at least one product, (ii) crack heavies formed in or introduced into said second reaction zone and (iii) vaporize at least a portion of said at least one product upon production thereof, wherein less than about 1 weight percent water is present in the second reaction zone;
    c. withdrawing an overhead vapor fraction from said second reaction zone, said overhead vapor fraction comprising said at least one product, and introducing at least a portion of said withdrawn overhead vapor fraction into at least one condensation zone to produce said at least one product in the liquid phase;
    d. withdrawing a liquid fraction from said at least one condensation zone, said liquid fraction comprising said at least one product and water, and introducing at least a portion of said withdrawn liquid fraction into at least one separation zone to provide by phase separation an organic liquid fraction comprising said at least one product and an aqueous liquid fraction comprising water;
    e. withdrawing said organic liquid fraction from said at least one separation zone, said organic liquid fraction comprising said at least one product, and introducing at least a portion of said withdrawn organic liquid fraction into at least one reactant recovery distillation zone to provide an overhead fraction comprising said at least one reactant and a bottoms liquid fraction comprising said at least one product;
    f. withdrawing said bottoms liquid fraction from said at least one reactant recovery distillation zone, said bottoms liquid fraction comprising said at least one product, and introducing at least a portion of said withdrawn bottoms liquid fraction into at least one product recovery distillation zone to provide an overhead fraction comprising said at least one product and a bottoms liquid fraction comprising heavies; and
    g. recovering said at least one product from said withdrawn overhead fraction.

2. The process of claim 1 wherein in step (a) said at least one reactant comprises a crude acrylic acid stream containing acrylic acid dimer and/or other Michael-addition heavies, and an alcohol-containing feedstock comprising a crude 2-ethylhexanol stream.

3. The process of claim 1 wherein said at least one reactant comprises a carboxylic acid-containing feedstock and/or an alcohol-containing feedstock generated from a heavy residue-containing stream from another process which employs an equilibrium-limited reaction.

4. The process of claim 1 wherein said product is represented by the formula R'C(O)OR''', said reactant is represented by the formula R'C(O)OH, and another said reactant is represented by the formula R'''OH wherein R' is a hydrocarbyl-containing group of 1 to about 8 carbon atoms and R''' is a hydrocarbyl-containing group of 4 to about 12 carbon atoms.

5. The process of claim 1 in which butyl acrylate and 2-ethylhexyl acrylate are simultaneously produced.

6. The process of claim 1 in which the catalyst comprises a sulfuric acid, a sulfonic acid or an acidic exchange resin.

7. The process of claim 1 wherein the equilibrium-limited reaction is an esterification of a carboxylic acid of 2 to 4 carbons with an alcohol of 4 to about 12 carbons.

8. The process of claim 7 wherein the carboxylic acid comprises acrylic acid and the alcohol comprises 2-ethylhexanol.

9. A process for conducting an equilibrium-limited reaction of at least one reactant to produce at least one product, comprising:
    a. reacting said at least one reactant in a first reaction zone maintained under reaction conditions, including temperature and pressure, sufficient to produce said at least one product and sufficient to maintain at least a portion of said at least one reactant and said at least one product in the liquid phase;
    b. withdrawing a liquid fraction containing said at least one reactant and said at least one product from said first reaction zone, and introducing at least a portion of said withdrawn liquid fraction into a second reaction zone maintained under reaction conditions, including temperature and pressure, sufficient to (i) produce said at least one product, (ii) crack heavies formed in or introduced into said second reaction zone and (iii) vaporize at least a portion of said at least one product upon production thereof, wherein less than about 1 weight percent water is present in the second reaction zone;
    c. withdrawing an overhead vapor fraction from said second reaction zone, said overhead vapor fraction comprising said at least one product, and introducing at least a portion of said withdrawn overhead vapor fraction into at least one condensation zone to produce said at least one product in the liquid phase, and introducing at least one polymerization inhibitor into said at least one condensation zone;
    d. withdrawing a liquid fraction from said at least one condensation zone, said liquid fraction comprising said at least one product and water, and introducing at least a portion of said withdrawn liquid fraction into at least one separation zone to provide by phase separation an organic liquid fraction comprising said at least one product and an aqueous liquid fraction comprising water;
    e. withdrawing said organic liquid fraction from said at least one separation zone, said organic liquid fraction comprising said at least one product, and introducing at least a portion of said withdrawn organic liquid fraction into at least one reactant recovery distillation zone to provide an overhead fraction comprising said at least one reactant and a bottoms liquid fraction comprising said at least one product, and introducing at least one polymerization inhibitor into said at least one reactant recovery distillation zone;

f. withdrawing said bottoms liquid fraction from said at least one reactant recovery distillation zone, said bottoms liquid fraction comprising said at least one product, and introducing at least a portion of said withdrawn bottoms liquid fraction into at least one product recovery distillation zone to provide an overhead fraction comprising said at least one product and a bottoms liquid fraction comprising heavies, and introducing at least one polymerization inhibitor into said at least one product recovery distillation zone;

g. withdrawing from said at least one product recovery distillation zone a bottoms fraction comprising at least one polymerization inhibitor and supplying at least a portion of the withdrawn bottoms fraction to said at least one condensation zone, said at least one reactant recovery distillation zone, said at least one product recovery distillation zone and a water removal distillation zone, in an amount sufficient to minimize or eliminate polymerization of said at least one reactant and said at least one product; and h. recovering said at least one product from said withdrawn overhead fraction.

10. A process for conducting an equilibrium-limited reaction of at least one reactant to produce at least one product, comprising:

a. reacting said at least one reactant in a first reactor maintained under reaction conditions, including temperature and pressure, sufficient to produce said at least one product and sufficient to maintain at least a portion of said at least one reactant and said at least one product in the liquid phase;

b. withdrawing a liquid fraction containing said at least one reactant and said at least one product from said first reactor, and introducing at least a portion of said withdrawn liquid fraction into a second reactor maintained under reaction conditions, including temperature and pressure, sufficient to (i) produce said at least one product, (ii) crack heavies formed in or introduced into said second reactor and (iii) vaporize at least a portion of said at least one product upon production thereof, wherein less than about 1 weight percent water is present in the second reactor;

c. withdrawing an overhead vapor fraction from said second reactor, said overhead vapor fraction comprising said at least one product, and introducing at least a portion of said withdrawn overhead vapor fraction into at least one condensation zone to produce said at least one product in the liquid phase;

d. withdrawing a liquid fraction from said at least one condensation zone, said liquid fraction comprising said at least one product and water, and introducing at least a portion of said withdrawn liquid fraction into at least one separation zone to provide by phase separation an organic liquid fraction comprising said at least one product and an aqueous liquid fraction comprising water;

e. withdrawing said organic liquid fraction from said at least one separation zone, said organic liquid fraction comprising said at least one product, and introducing at least a portion of said withdrawn organic liquid fraction into at least one reactant recovery distillation zone to provide an overhead fraction comprising said at least one reactant and a bottoms liquid fraction comprising said at least one product;

f. withdrawing said bottoms liquid fraction from said at least one reactant recovery distillation zone, said bottoms liquid fraction comprising said at least one product, and introducing at least a portion of said withdrawn bottoms liquid fraction into at least one product recovery distillation zone to provide an overhead fraction comprising said at least one product and a bottoms liquid fraction comprising heavies; and g. recovering said at least one product from said withdrawn overhead fraction.

11. The process of claim 10 wherein said product is represented by the formula R'C(O)OR''', said reactant is represented by the formula R'C(O)OH, and another said reactant is represented by the formula R'''OH wherein R' is a hydrocarbyl-containing group of 1 to about 8 carbon atoms and R''' is a hydrocarbyl-containing group of 4 to about 12 carbon atoms.

12. The process of claim 10 wherein the catalyst comprises a sulfuric acid, a sulfonic acid or an acidic exchange resin.

13. The process of claim 10 wherein less than about 1 weight percent water is present in the second reaction zone.

14. The process of claim 10 wherein the equilibrium-limited reaction is an esterification of a carboxylic acid of 2 to 4 carbons with an alcohol of 4 to about 12 carbons.

15. The process of claim 14 wherein the carboxylic acid comprises acrylic acid and the alcohol comprises n-butanol.

16. The process of claim 10 wherein the carboxylic acid comprises acrylic acid and the alcohol comprises 2-ethylhexanol.

* * * * *

UNITED STATES PATENT AND TRADEMARK OFFICE
CERTIFICATE OF CORRECTION

| | | |
|---|---|---|
| PATENT NO. | : 7,569,721 B2 | Page 1 of 1 |
| APPLICATION NO. | : 10/544817 | |
| DATED | : August 4, 2009 | |
| INVENTOR(S) | : Patterson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this
Tenth Day of May, 2011

David J. Kappos
*Director of the United States Patent and Trademark Office*